US012263348B2

(12) United States Patent
Tolani et al.

(10) Patent No.: US 12,263,348 B2
(45) Date of Patent: Apr. 1, 2025

(54) CIRCADIAN RHYTHM MONITORING AND REGULATION SYSTEM

(71) Applicants: Intelligent Automation, LLC, Rockville, MD (US); Rensselaer Polytechnic Institute, Troy, NY (US)

(72) Inventors: Devendra Tolani, Germantown, MD (US); Pedram Hovareshti, Rockville, MD (US); Rajeev Bhalla, Rockville, MD (US); Glenn Nickens, Clarksburg, MD (US); Jordan Specht, Gaithersburg, MD (US); Devon Callan, Olney, MD (US); Andrew Bierman, Albany, NY (US); Mariana G Figueiro, Troy, NY (US); Geoffrey E Jones, Manchester, CT (US); Mark S Rea, Melrose, NY (US); Gregory A Ward, Niskayuna, NY (US)

(73) Assignee: BLUEHALO LABS, LLC, Albuquerque, NM (US)

( * ) Notice: Subject to any disclaimer, the term of this patent is extended or adjusted under 35 U.S.C. 154(b) by 119 days.

(21) Appl. No.: 16/888,083

(22) Filed: May 29, 2020

(65) Prior Publication Data

US 2020/0398076 A1 Dec. 24, 2020

Related U.S. Application Data

(60) Provisional application No. 62/855,443, filed on May 31, 2019.

(51) Int. Cl.
*A61N 5/06* (2006.01)

(52) U.S. Cl.
CPC .... *A61N 5/0618* (2013.01); *A61N 2005/0626* (2013.01); *A61N 2005/0648* (2013.01);
(Continued)

(58) Field of Classification Search
CPC .......... A61N 5/0618; A61N 2005/0626; A61N 2005/0648; A61N 2005/0652; A61N 2005/0663; A61N 2005/0662
See application file for complete search history.

(56) References Cited

U.S. PATENT DOCUMENTS 10,646,685 B2    5/2020   Rea et al.
2019/0098725 A1* 3/2019  Sadwick ................ H05B 45/20

FOREIGN PATENT DOCUMENTS

CN         107438398 A    * 12/2017   ............... A61B 3/16
WO    WO-2013184627 A1   * 12/2013   ........... A61B 5/4857
(Continued)

OTHER PUBLICATIONS

Circadian light by Mark S. Rea, Marianne G. Figueiro, Andrew Bierman and John D. Bullough as published in Journal of Circadian Rhythms 2010, 8:2.
(Continued)

*Primary Examiner* — Carl H Layno
*Assistant Examiner* — Aya Ziad Bakkar
(74) *Attorney, Agent, or Firm* — Amster, Rothstein & Ebenstein LLP

(57) ABSTRACT

A Circadian Rhythm Monitoring and Regulation (CMR) system and method that includes: a novel non-obtrusive wearable system for increasing the health and productivity of warfighters or other individuals that are disrupted by excessive, abnormal shifts in work or flights across multiple time zones. The CMR system is based on advanced sensor and software technology and models of human circadian system phototransduction and a circadian stimulator oscillator developed by applicants. It measures circadian misalignment and provides lighting suggestions for circadian rhythm maintenance and realignment.

20 Claims, 7 Drawing Sheets

(52) U.S. Cl.
CPC ............... *A61N 2005/0652* (2013.01); *A61N 2005/0663* (2013.01)

(56) References Cited

FOREIGN PATENT DOCUMENTS

| WO | WO-2016145059 A1 * | 9/2016 | ........ A61M 21/0094 |
|---|---|---|---|
| WO | WO-2017013051 A1 * | 1/2017 | |
| WO | WO-2018042218 A1 * | 3/2018 | |
| WO | WO-2018130546 A1 * | 7/2018 | ............ A61M 21/02 |

OTHER PUBLICATIONS

Quantifying Human Circadian Pacemaker Response to Brief, Extended, and Repeated Light Stimuli over the Phototopic Range by Richard E. Kronauer, Daniel B. Forger and Megan E. Jewett as published in Journal of Biological Rhythms, vol. 14 No. 6, Dec. 1999.

Modeling the spectral sensitivity of the human circadian system by Mark S. Rea, Mariana Figueiro, Andrew Bierman and R. Hamner as published in Lighting Research and Technology, Dec. 14, 2011.

A model of phototransduction by the human circadian system by Mark S. Rea, Mariana G. Figueiro, John D. Bullough and Andrew Bierman as published in Brain Research Reviews 50 (2005) 213-228.

* cited by examiner

CIRCADIAN RHYTHM MONITORING AND REGULATION SYSTEM

This non-provisional application claims priority from U.S. provisional patent application Ser. No. 62/855,443 filed on May 31, 2019, the complete disclosure of which is incorporated herein by reference.

This invention was made with government support under STTR Contract No. W911NF-16-C-0017 from US Army Research Office. The government has certain rights in the invention.

BACKGROUND OF THE INVENTION

This invention relates to a circadian rhythm monitoring and regulation system and method, and in particular, to a circadian rhythm monitoring and regulation system and method that can monitor and correct or maintain the circadian phase that participants are in, especially those that are involved in nighttime activities.

All mammals, including human beings, have a master clock residing in the suprachiasmatic nuclei (SCN) of the hypothalamus that orchestrates the timing of every peripheral clock in the body which, in turn, governs biological functions ranging from those performed by single cells (e.g., DNA repair) to those that control complex behavior patterns (e.g., sleep)1. These many orchestrated biological functions should be performed at specific times during the "expected", 24-hour light-dark cycle.

The adaptation to the Earth's 24-hour pattern of daylight and darkness by evolving biological rhythms is called circadian rhythms, which repeat at approximately 24-hour intervals. The misalignment of circadian rhythms has potential detrimental consequences such as increased sleepiness and decreased attention span during the day, lower productivity, and gastrointestinal disorders. Circadian rhythm misalignment is of great concern in military personnel. Correction or maintenance of circadian phase is critical for Servicemembers participating in military night operations or planning for trans-meridian flights. Circadian rhythm misalignment in military personnel is known to affect judgment, psychomotor skills, and may lead to or worsen symptoms of Post-Traumatic Stress.

Disruption of entrainment by "unexpected" light-dark exposure patterns compromises performance, physiology, and, over extended time, health. This can be of particular concern to soldiers, who must be able to perform optimally during any time of day including night operations. Most importantly, soldiers need to keep their circadian system entrained in the presence of long night/day operations as well as other disturbances. There is a special concern about circadian rhythm misalignment in military personnel as it is known to affect judgment, psychomotor skills, and may lead to or be triggered by Post-Traumatic Stress Disorder (PTSD). Many veterans who suffer from chronic pain resulting from war injuries, PTSD and/or traumatic brain injury (TBI) complain of some kind of sleep disturbances. An increasing body of research suggests that circadian misalignment plays a role in sleep disturbances experienced by this population. Even if circadian disruption is not the primary cause of the sleep disturbances in PTSD patients, similar to patients with Alzheimer's disease, the disrupted sleep aggravates patients' exposure to irregular light/dark patterns, which can in turn lead to circadian disruption and subsequently result in more sleep disturbances.

Currently, there exist commercial off-the-shelf (COTS) devices that monitor human activity and physiological signals such as pulse rate, body temperature etc. However, these devices do not directly estimate the circadian rhythm, and more importantly, do not measure the human light exposure. There are also COTS devices that provide blue light to affect circadian rhythm, but they are self-administered and not tied to measurement devices for optimum circadian light exposure control. A good example is Philips goLITE BLUE™ energy light: which is available at http://www.usa.philips.com/c-p/HF3332_60/golite-blu-energy-light.

Other references discussing circadian rhythm and its effects on the human system and attempts to alter it include: Kronauer R E, Forger D B, Jewett M E. 1999. *Quantifying human circadian pacemaker response to brief, extended, and repeated light stimuli over the photopic range*. J. Biol Rhythms. 1999; 14:6; Rea M S, Figueiro M G, Bierman A, Bullough J D. Circadian light. J. Circadian Rhythms. 2010; 8:2; Rea M S, Figueiro M G, Bierman A, Hamner R. *Modeling the spectral sensitivity of the human circadian system*. Light Res Tech. 2012; 44(4): 386-396; and Rea M S, Figueiro M G, Bullough J D, Bierman A. *A model of phototransduction by the human circadian system*. Brain Res Rev. 2005; 50(2):213-228, the complete disclosures of which are incorporated herein by reference.

Another reference of interest is U.S. Pat. No. 10,646,685 to Rea et al., which discloses a Luminous Roof for NICU Incubators for Regulating Circadian Rhythms in Infants and for Providing High Visibility of infant anatomy for Healthcare Staff. In some examples, the lighting system includes a camera coupled to a sheet of flexible material configured to capture at least one image of an object synchronously with the light emitted by a plurality of light sources Heretofore, though, there has been no comprehensive unobtrusive and easy-to-use solution that measures the circadian misalignment and automatically administers the appropriate therapy for realignment of circadian rhythm.

SUMMARY OF THE INVENTION

To address this challenge presented by circadian rhythm misalignment, the subject invention is an, has been developed to provide a Circadian Rhythm Monitoring and Regulation (CMR) system and method that includes: a novel, low-cost, non-obtrusive wearable system for increasing the health and productivity of warfighters or other individuals that are disrupted by excessive, abnormal shifts in work or flights across multiple time zones. The CMR system is based on advanced sensor and software technology and models of human circadian system phototransduction and a circadian stimulator oscillator developed by applicant. It measures circadian misalignment and provides lighting suggestions for circadian rhythm maintenance and realignment.

In one embodiment, a system having circadian rhythm monitoring and regulation capabilities is provided that includes a light sensor, the light sensor worn by a user near eye level thereof to collect calibrated, ecological light-dark exposure patterns; an activity sensor, worn by the user to collect indicators of activity; a mobile computing device having an App that connects to the sensors and computes light recommendation treatment for the user, based the collected light-dark exposure patterns and collected indictors of activity; and light therapy treatment googles worn by the user at recommended times and intervals as established by the App.

The system can include the light sensor and activity sensor being wirelessly connected to the mobile computing device. The App can include a circadian stimulator oscillator to deliver a light prescription to delay or advance a circadian phase of the user. and the App may incorporate a modified Kronauer model of human circadian entrainment.

The system may include using dim light melatonin onset (DMLO) as a marker of circadian phase, and saliva samples can be collected from the user for DMLO measurement.

The system may continuously monitor circadian stimulus using the light sensor and may continuously monitor physiological signals using the activity sensor. The system can use personal light exposures detected by the light sensor to predict circadian phases. Phase shifts can be determined from time of day differences of when the angular positions occur on a circadian stimulator oscillator model, and the light therapy goggles can include blue LED lights that are worn by the user when instructed by the App. The system can also include orange-tinted glasses worn by the user as instructed by the App.

In another embodiment of the invention, a method of monitoring and regulating circadian rhythm is provided including the steps of providing a light sensor; a user wearing the light sensor near eye level to collect calibrated, ecological light-dark exposure patterns; providing an activity sensor; the user wearing the activity sensor to collect indicators of activity; providing a mobile computing device having an App that is connected to the sensors; computing light recommendation treatment for the user, based on collected light-dark exposure patterns and collected indictors of activity; providing light therapy treatment goggles; and the user wearing the light treatment goggles at recommended times and intervals as established by the App.

The method of monitoring and regulating circadian rhythm can also include the steps of providing a circadian stimulator oscillator in the App; and delivering a light prescription to delay or advance a circadian phase of the user. The method of monitoring and regulating circadian rhythm can also include the steps of continuously monitoring circadian stimulus using the light sensor; and continuously monitoring physiological signals using the activity sensor.

The method of can also include the step of determining phase shifts from time of day differences of when the angular positions occur on a circadian stimulator oscillator model. The method can further include the steps of providing blue LED lights in the light therapy goggles; and the user wearing the light therapy goggles when instructed by the App. Also, the method of monitoring and regulating circadian rhythm can include the steps of providing orange-tinted glasses; and the user wearing the orange-tinted glasses when instructed by the App.

The method of monitoring and regulating circadian rhythm may further include the steps of detecting personal light exposures using the light sensor; and predicting circadian phases using the detected light exposures. The method can additionally include the steps of using dim light melatonin onset (DMLO) as a marker of circadian phase; and collecting saliva samples from the user for DMLO measurement.

BRIEF DESCRIPTION OF THE DRAWINGS

The above-mentioned and other features and objects of this invention and the manner of obtaining them will become more apparent, and the invention itself will be better understood by reference to the following description of embodiments of the present invention taken in conjunction with the accompanying figures, wherein.

Figure 1:
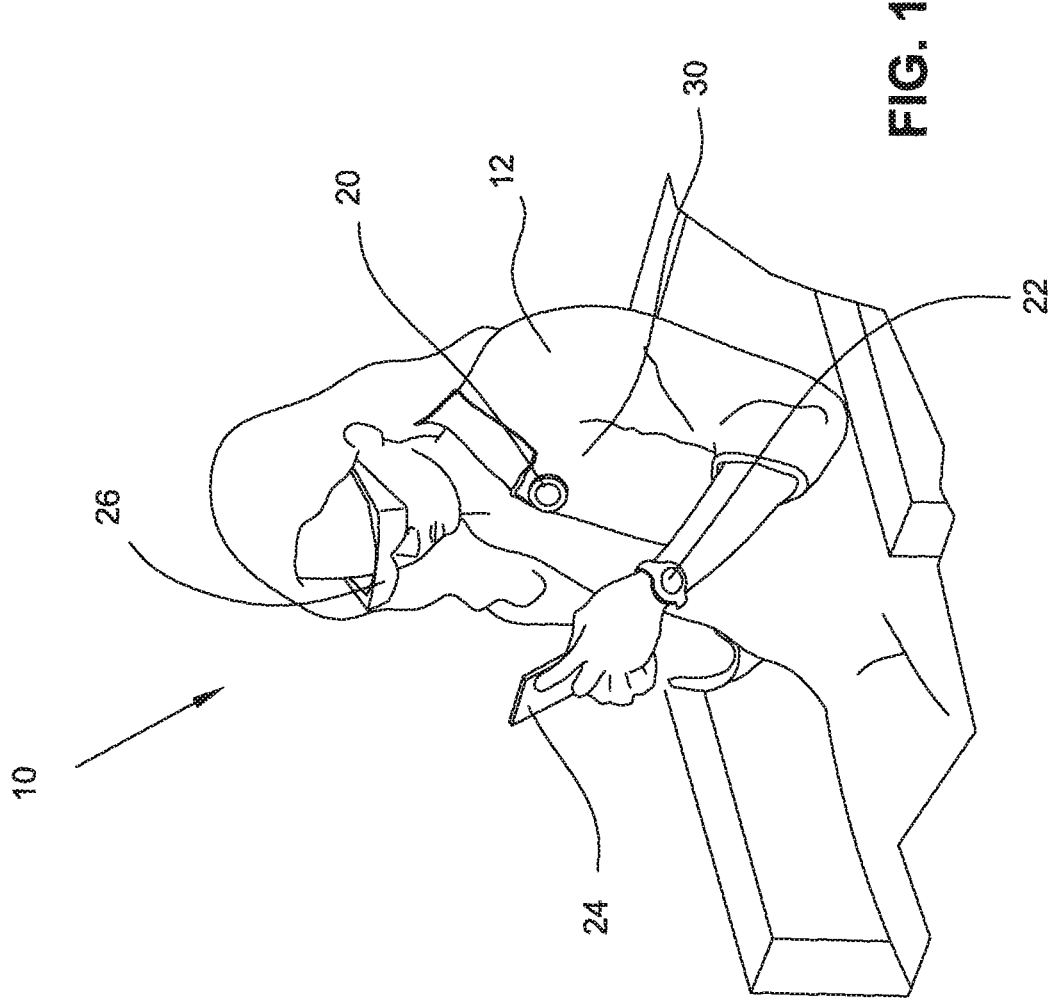
FIG. 1 shows a patient participating in a CMR exercise utilizing parts of the system including a light sensor button, an activity sensor worn on the wrist, a mobile phone with a CMR app, and light treatment goggles.

Corresponding reference characters indicate corresponding parts throughout the several views. Although the figures represent embodiments of the present invention, the figures are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF EMBODIMENTS OF THE INVENTION

For the purpose of promoting an understanding of the principles of the invention, reference will now be made to the embodiments illustrated in the drawing, which are described below. It will nevertheless be understood that no limitation of the scope of the invention is thereby intended. The invention includes any alterations and further modifications in the illustrated devices and described methods and further applications of the principles of the invention, which would normally occur to one skilled in the art to which the invention relates.

Figure 4:
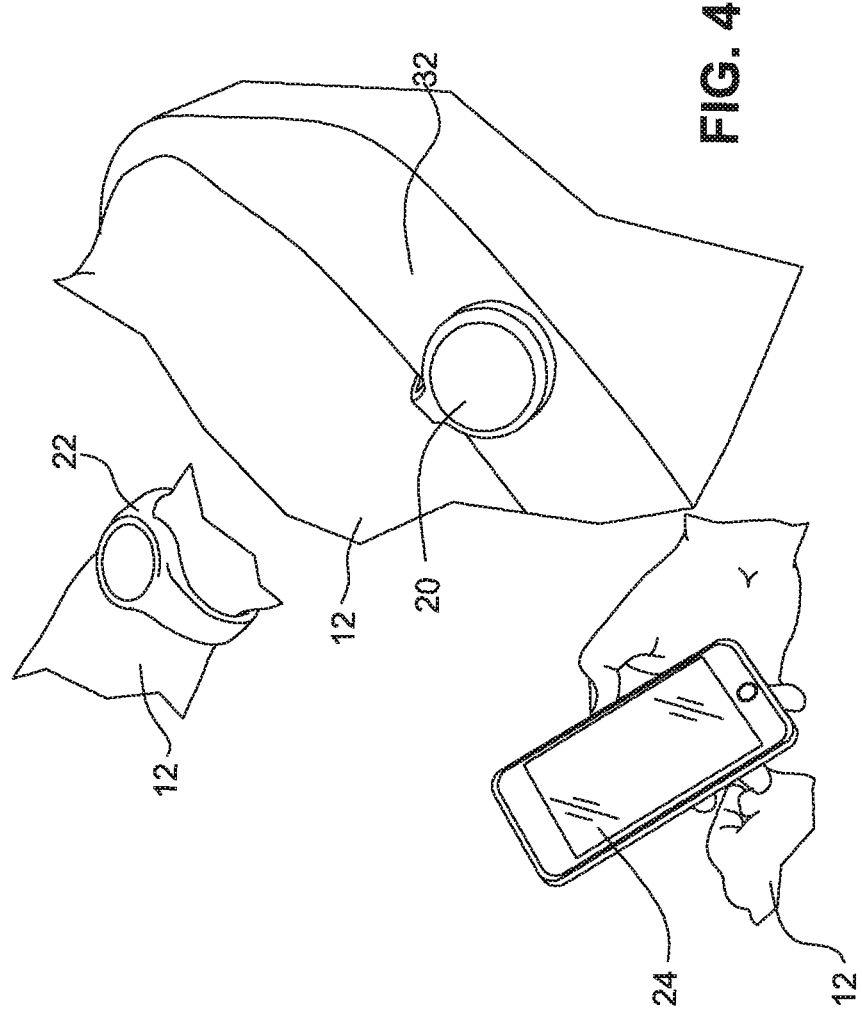
FIG. 4 are enlarged photos of the light sensor button, activity sensor worn on the wrist, and the mobile phone with a CMR app shown opened on the screen of FIG. 1.

Now referring to FIGS. 1 and 4, parts of a Circadian Rhythm Monitoring and Regulation (CMR) system and method are shown, generally indicated as 10 being utilized by an individual or user 12. In one embodiment, CMR system and method 10 includes a light sensor button 20, an activity sensor 22 worn on the wrist, a mobile phone with a CMR App 24, and light treatment goggles 26. The system 10 can continuously monitor circadian stimulus (CS) and physiological signals, quantify circadian entrainment/disruption and use a predictive model to compute light treatments.

In the embodiment shown, light sensor button 20 is a clip-on device designed to be worn near the eye level, such as on a collar or lapel of a user's apparel 30 or 32, to collect calibrated, ecological light-dark exposure patterns. The activity sensor 22 is a watch type device, worn on the wrist of user 12. Activity sensor 22 includes collecting indicators of activity. The sensing function of this device can be complemented with chest strap heart rate sensors (not shown) that are well known. In one embodiment, a modified Kronauer model of human circadian entrainment (circadian stimulus, CS-oscillator model) was incorporated into the App to deliver a light prescription to advance or delay circadian phase. The CS-oscillator model uses personal light exposure to predict circadian phase (see Figures).

The mobile phone with CMR App 24 is a known type of smartphone and the App that connects to the sensors and computes light recommendation or treatments for delivery by light treatment goggles 26. In one embodiment, the phone App is connected to the light and activity sensor via Bluetooth. Light treatment goggles 26 are designed to provided light therapy. Alternately, the mobile phone and CMR App 24 can use environmental light for light regulation instead of or in addition to light treatment goggles 26.

Figure 2:
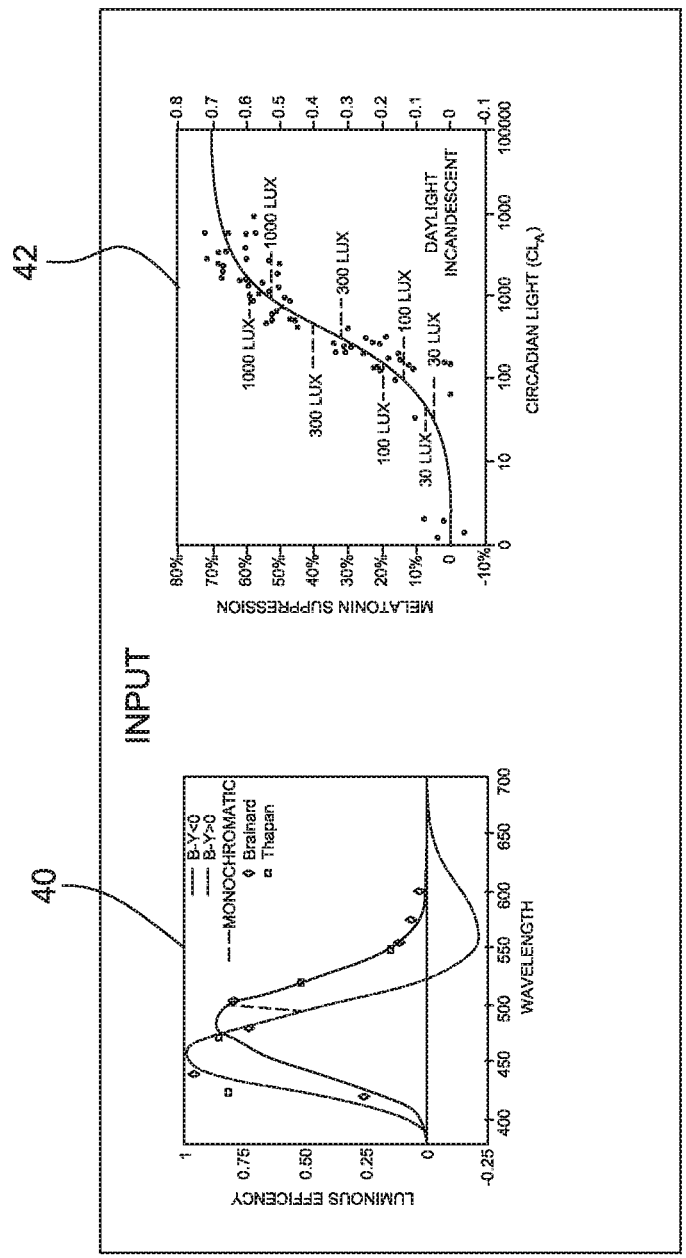
FIG. 2 are Input graphs of phototransduction efficiency for suppressing nocturnal melatonin from monochromatic stimuli and circadian stimulus being proportional to percent nocturnal melatonin suppression from threshold to saturation.

Referring to FIG. 2, Input graphs are shown. The first graph 40 depicts luminous efficiency in relation to wavelength, and the second graph 42 depicts melatonin suppression in relation to circadian light. The circadian stimulus is shown proportional to the percent of nocturnal melatonin suppression from threshold to saturation, as a function of circadian light. The first graph 40 shows the phototransduction efficiency for suppressing nocturnal melatonin from monochromatic stimuli and basis for quantifying circadian light (CLA). The second graph 42 shows the Circadian stimulus (CS) is proportional to the percent of nocturnal melatonin suppression from threshold to saturation as a function of CLA.

Figure 3:
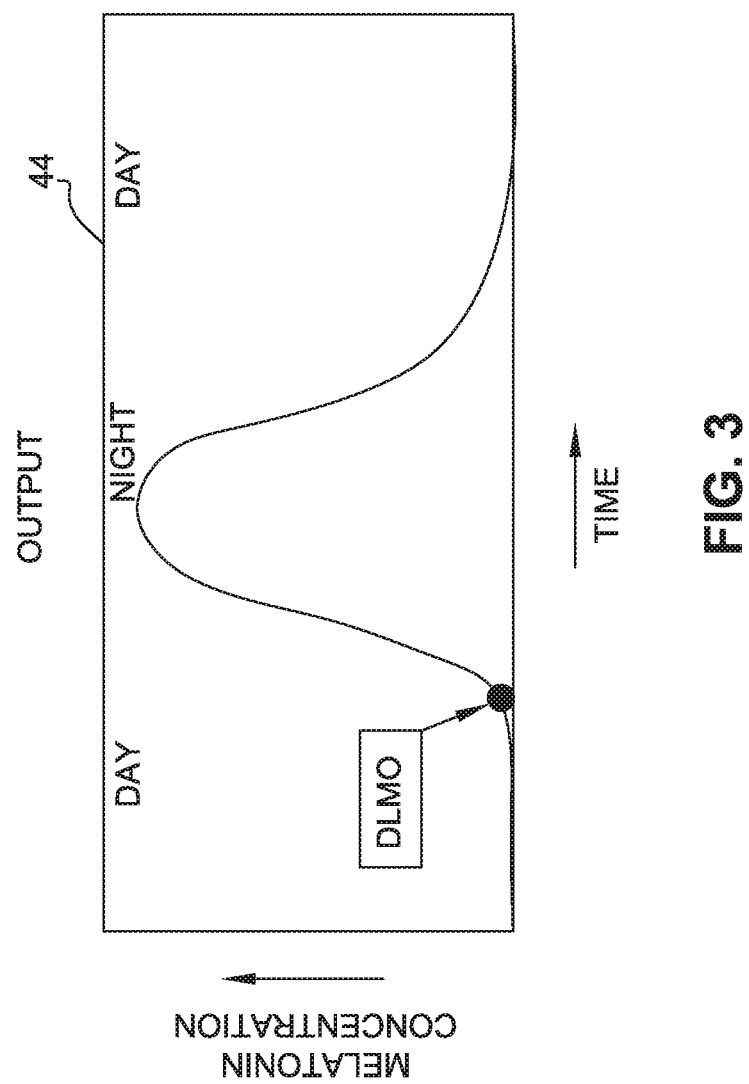
FIG. 3 is an Output graph showing dim light onset in relation to time of day.

Referring to FIG. 3, an Output graph 44 is shown wherein dim light melatonin onset (DMLO) can be used as a marker of circadian phase. DMLO is the time in the evening in which melatonin levels rise above certain threshold. A model of human circadian entrainment (circadian stimulator oscillator) was incorporated into the App to deliver a light prescription to advance or delay circadian phase. The circadian stimulator oscillator uses personal light exposures detected by light sensor 20 to predict circadian phase. The phone App is connected to light sensor 20 and activity sensor 22 via Bluetooth.

Figure 5:
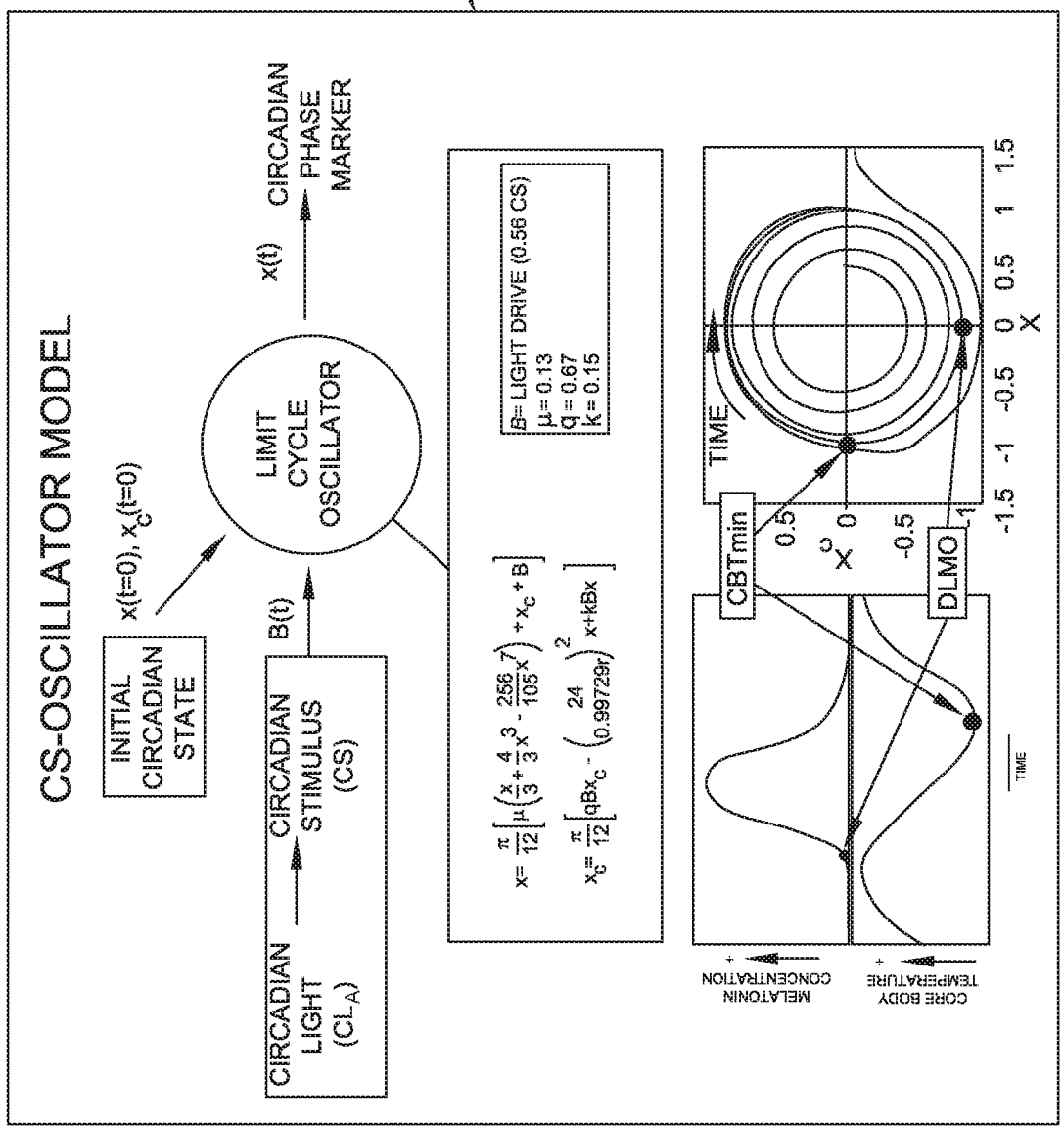
FIG. 5 is a diagram of the operation of a circadian stimulator oscillator model used with the CMR.

Referring to FIG. 5, a circadian stimulator oscillator model is generally depicted as 46 and shows how an initial circadian state can be phase shifted by applying circadian light stimulus. Phase markers, such as minimum body core temperature (CBTmin) and DLMO, correspond to particular angular positions in a plot of the oscillator variables. Phase shifts are determined from time of day differences when the angular positions occur.

Figure 7:
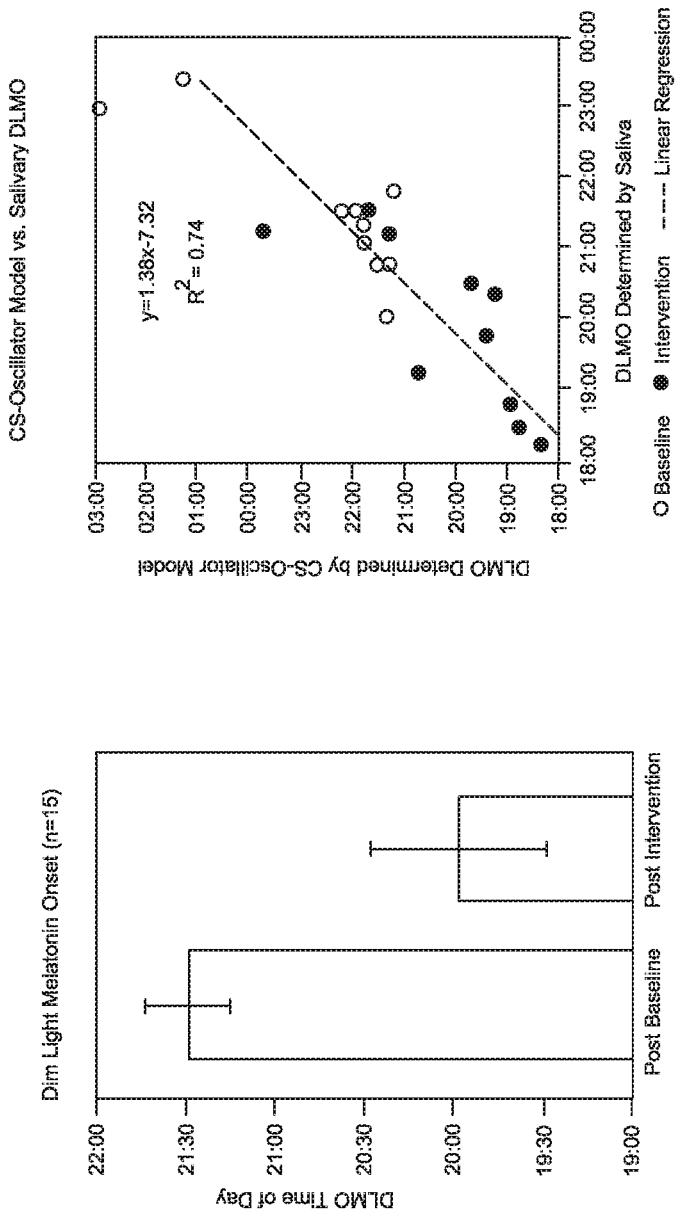
FIG. 7 shows a graph of dim light melatonin onset time variance from treatment with the CMR and a graph of predicted and actual dim light melatonin onset.

In one embodiment the CMR system and method continuously monitors circadian stimulus using light sensor 20 and physiological signals using activity sensor 22. The quantity of circadian entrainment/disruption is determined, and predictive models are used (see FIG. 7) to compute light treatments to be provided by mobile phone and CMR App 24 and light treatment goggles 26. In the graph of DMLO (n=15), the average time of DMLO as determined from periodic saliva samples at the end of baseline (week 2) and at the end of intervention (week 4), as discussed by testing described below. In the CS-Oscillator Model verses Salivary DMLO graph of FIG. 7, the predicted and actual individual DMLO times at the end of baseline and at the end of intervention are shown. The dashed line is the best fitting linear relationship between predicted and actual ($R^2$=0.74).

Figure 6:
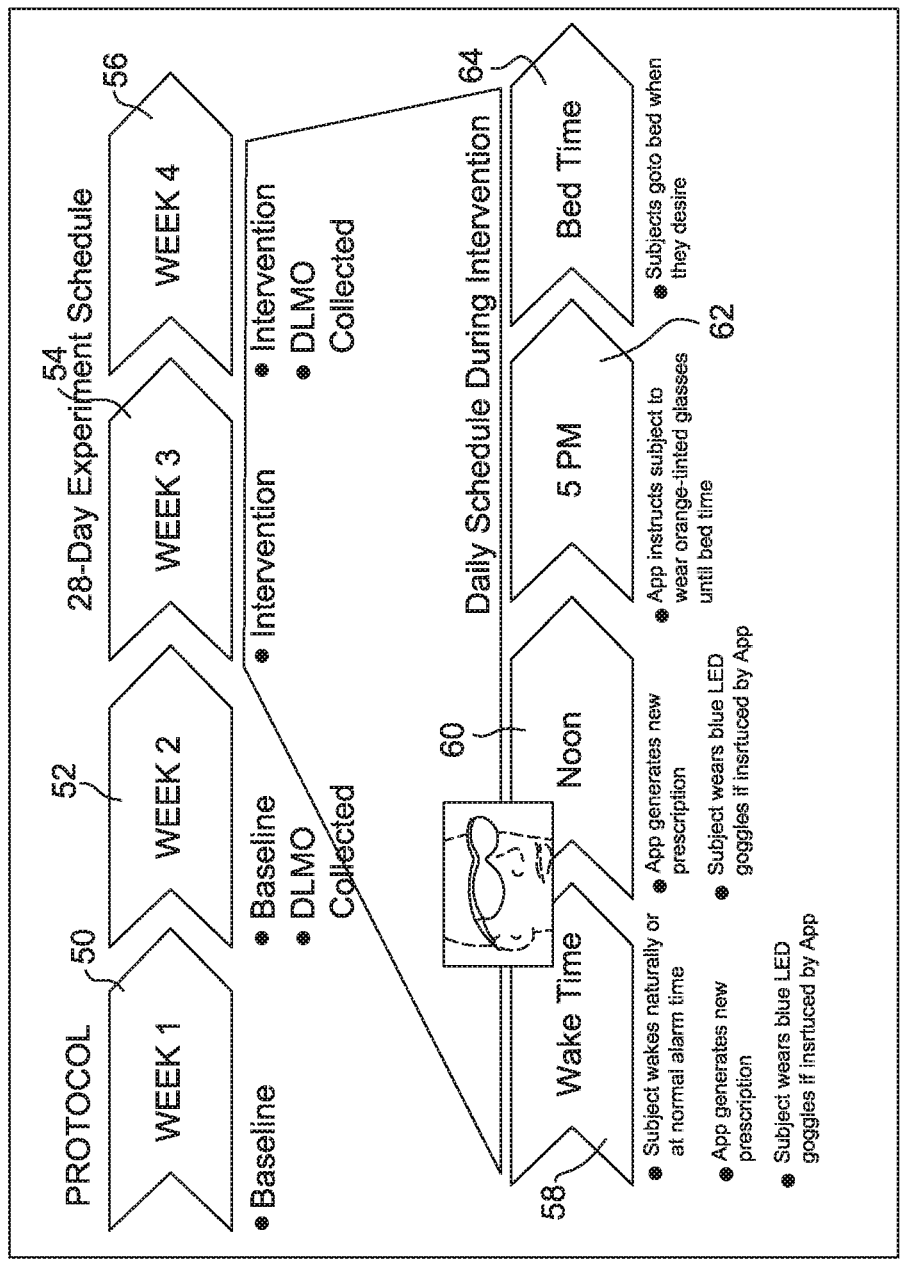
FIG. 6 shows a diagram of an experimental protocol used with the subject.

Now referring to FIG. 6, one test of the CMR system and method 10, included sixteen subjects. Saliva samples were collected from 15 subjects (the subjects included 10 females, and 5 males aged 18 to 32 years old) and data from the system was obtained from 11 subjects. Light and activity data were collected for 14 days immediately before the 14 intervention days to form a baseline. As shown by Week One 50 and Week Two 52 in FIG. 6. Data was also collected during the 14 day intervention time period as shown by Weeks Three 54 and Week Four 56. Saliva samples were collected for DMLO measurement at the conclusion of the baseline period and the intervention period. Also shown in FIG. 6, is that during Wake Time 58 the subject 12 woke naturally or at normal alarm times. The App of phone 24 generated a new prescription and the subject 12 wore blue LED goggles if instructed to do so by the App. Then, at Noon 60, the App generated a new prescription and the subject 12 wore blue LED goggles if instructed to do so by the App. Also shown in FIG. 6 is a 5 PM time 62, wherein the App instructed the subject 12 to wear orange-tinted glasses until bed time. Lastly, FIG. 6 depicts the Bed Time 64 cycle wherein subject 12 went to bed when desired.

Based upon the DMLO's measured right after the baseline time and right after the 14 day intervention time, all subjects 12 advanced their circadian phase. Additional phase change should be able to be achieved by altering sleep and wake times. Accordingly, the sample test proved that the CMR system using the circadian stimulator oscillator model can predict changes in circadian phase based upon actual light exposures.

It has been determined that the subject invention provides a circadian monitoring and regulation system (CMR) 10 that includes the features of being compact, lightweight, and a low maintenance system design. CMR 10 is also provides non-obtrusive, effective, continuous, and 'at-ease' measurement of circadian biomarkers including activity, calibrated circadian light, heart rate. CMR system 10 has precise and low complexity embedded biomarker processing algorithms and includes an easy-to-use mobile software application for computing circadian misalignment and providing treatment prescription in real time. The App of mobile phone 10 provides for storage of sensor readings with email capability for post-processing. CMR 10 provides safe light treatment delivery via goggles 26, which utilizes inexpensive LED technology and utilizes wireless data exchange with sensors 20 and 22.

Applicants have developed novel functionality and conducted significant research and development on the subject invention. CMR 10 includes upgraded sensors, customizing capabilities, wireless mode of operation, data syncing, recording, and reporting to remote system of management. CMR 10 functions with all Commercially-Off-The-Shelf (COTS) Bluetooth low energy (BLE) enabled heartrate sensors as an additional modality.

A mathematical model of human circadian phototransduction has been developed and validated. It provides the ability to estimate circadian stimulus (CS) from a light source with any power spectral distribution and use CS as input to the circadian system model to quantify the effectiveness of various light sources on the circadian system.

CMR 10 provides a wearable prototype working with a mobile Software Application (app). The app can be seamlessly installed and run on smartphones. A cross-platform version of the App has also been developed, so that in case of need, it can be customized and used with Android phones.

Field data have been collected and successfully demonstrated the ability of the model to predict phase shifting of dim light melatonin onset (DLMO) after a lighting intervention. Additional confirmation of the ability of CMR 10 to predict phase shifting has been obtained, using the new hardware and associated App. It is believed that utilizing the invention, further potentials exist to increase the circadian phase shifting associated with phase shifting and additional sensors.

An integrated compact, lightweight, and low maintenance system was developed. The CMR system 10 was proven and improved by human subject studies and conducted extensive lab testing and iterative design modification has been conducted.

The invention has been taught with specific reference to these embodiments, one skilled in the art will recognize that changes can be made in form and detail without departing from the spirit and scope of the invention. For instance, although, in the embodiment shown the CMR utilizes a mobile smartphone, it should be appreciated that the invention may be used with other computing devices such as a computer tablet, laptop computer or desktop computer and the mobile computing device as used herein includes any computing device and the App includes any software for use thereon. Also, goggles as used herein can include other light delivery systems to accomplish the same objective. This application is intended to cover any variations, uses, or adaptations of the invention using its general principles. Further, this application is intended to cover such departures from the present disclosure as has come within the known or customary practice in the art to which the invention pertains and which fall within the limits of the appended claims or equivalents thereof.

The invention claimed is:

1. A system comprising:
   a light sensor, configured to be worn on a torso of a user to collect light information associated with calibrated, ecological light-dark exposure patterns;
   an activity sensor, configured to be worn by the user to collect activity information associated with activity of the user;
   a pair of light therapy treatment goggles configured to be worn on a head of the user, the pair of light therapy treatment goggles comprising blue LED lights;
   orange-tinted glasses configured to be worn on the head of the user; and,
   a mobile computing device located remotely from the light sensor, the activity sensor and the pair of light therapy treatment goggles, wherein the mobile computing device communicates with the light sensor and the activity sensor, wherein the mobile computing device comprises a mobile application stored in memory including processor executable instructions, that when executed by a processor of the mobile computing device operably connected to the memory, computes a circadian light stimulus light treatment recommendation for the user, based on the collected light information associated with calibrated, light-dark exposure patterns and activity information, the circadian light stimulus light treatment recommendation being instructions for delivery of light therapy to the user in the form of blue light by the blue LED lights of the pair of light therapy treatment goggles worn by the user as instructed by the mobile application at first recommended times and intervals and blockage of blue light provided by the orange-tinted glasses worn by the user as instructed by the mobile application at second recommended times and intervals;
   wherein the circadian light stimulus light treatment recommendation comprises instructions to the user to wear the pair of light therapy treatment goggles or the orange-tinted glasses at the respective first and second recommended times and intervals so that the user is exposed to blue light by the blue LED lights of the pair of light therapy treatment goggles and blocked from blue light by the orange-tinted glasses as part of the light therapy; and,
   wherein the pair of light therapy treatment goggles and the orange tinted-glasses provide lighting intervention during the respective first and second recommended times and intervals.

2. The system as set forth in claim 1, wherein the light sensor and activity sensor are wirelessly connected to the mobile computing device.

3. The system as set forth in claim 1, wherein the mobile application includes processor executable code that when executed by the processor implements a circadian stimulator oscillator to deliver a light prescription to delay or advance a circadian phase of the user.

4. The system as set forth in claim 1, wherein the mobile application uses a modified Kronauer model of human circadian entrainment.

5. The system as set forth in claim 1, wherein dim light melatonin onset (DLMO) is used as a marker of circadian phase.

6. The system as set forth in claim 5, wherein saliva samples are collected from the user for DMLO measurement.

7. The system as set forth in claim 1, wherein the light sensor continuously collects light information.

8. The system as set forth in claim 7, wherein the activity sensor continuously collects activity information.

9. The system as set forth in claim 1, wherein the system uses personal light exposures detected by the light sensor to predict circadian phases, and the mobile computing device determines a solar phase.

10. The system as set forth in claim 9, wherein phase shifts are determined from time of day differences when angular positions occur on a circadian stimulator oscillator model.

11. The system as set forth in claim 1, wherein the pair of light therapy goggles are worn by the user when instructed by the mobile application.

12. The system as set forth in claim 11, wherein the orange-tinted glasses are worn by the user when instructed by the mobile application.

13. A method comprising the steps of: providing a light sensor configured to be worn on a torso of a user to collect light information associated with calibrated, ecological light-dark exposure patterns; providing an activity sensor worn by the user to collect activity information associated with activity of the user; providing a pair of light therapy treatment goggles configured to be worn on a head of the user, the pair of light therapy treatment goggles comprising blue LED lights; providing orange-tinted glasses and, providing a mobile computing device, located remotely from the light sensor, the activity sensor and the pair of light therapy treatment goggles; using the mobile computing device to: communicates with the light sensor and the activity sensor, wherein the mobile computing device comprises a mobile application stored in memory and processor executable instructions, that when executed by a processor of the mobile computing device operably connected to the memory, causes the mobile application to: compute a circadian light stimulus light treatment recommendation for the user, based on the collected light information associated with calibrated, light-dark exposure patterns and activity information, the circadian light stimulus light treatment recommendation being instructions for delivery of light therapy to the user in the form of blue light by the blue LED lights of the pair of light therapy treatment goggles worn by the user as instructed by the mobile application at first recommended times and intervals and blockage of blue light provided by the orange-tinted glasses worn by the user as instructed by the mobile application at second recommended times and intervals; wherein the circadian light stimulus light treatment recommendation comprises: sending instructions to the user to wear the pair of light therapy treatment goggles or the orange-tinted glasses at the respective first and second recommended times and intervals so that the user is exposed to blue light by the blue LED lights of the pair of light therapy treatment goggles and blocked from blue light by the orange-tinted glasses as part of the light therapy; and, wherein the pair of light therapy treatment goggles and the orange tinted-glasses provide lighting intervention during the respective first and second recommended times and intervals.

14. The method as set forth in claim 13, further including the steps of:
providing a circadian stimulator oscillator in the mobile application; and
delivering a light prescription to delay or advance a circadian phase of the user.

15. The method as set forth in claim 13, further including the steps of:
continuously collecting light information using the light sensor;
continuously collecting activity information using the activity sensor; and
using the continuously collected light and activity information intermittently.

16. The method as set forth in claim 13, further including the step of determining phase shifts from time of day differences when angular positions occur on a circadian stimulator oscillator model.

17. The method as set forth in claim 13, further including the step of:
providing, by the mobile application, instructions to the user to wear the pair of light therapy goggles.

18. The method as set forth in claim 17, further including the steps of:
providing, by the mobile application, instructions to the user to wear the orange-tinted glasses at least partially during daytime.

19. The method as set forth in claim 13, further including the steps of:
collecting personal light exposures information using the light sensor; and
predicting circadian phases using the light exposure information.

20. The method as set forth in claim 13, further including the steps of:
using dim light melatonin onset (DLMO) as a marker of circadian phase; and
collecting saliva samples from the user for DLMO measurement.

* * * * *